United States Patent
Patil et al.

(10) Patent No.: US 11,534,553 B2
(45) Date of Patent: Dec. 27, 2022

(54) METHOD OF INJECTING OCTREOTIDE ACETATE INTO THE BODY

(71) Applicant: SUN PHARMACEUTICAL INDUSTRIES LIMITED, Maharashtra (IN)

(72) Inventors: Satyashodhan Babasaheb Patil, Vadodara (IN); Sudeep Kumar Agrawal, Vadodara (IN); Subhas Balaram Bhowmick, Vadodara (IN); Prashant Kane, Vadodara (IN)

(73) Assignee: SUN PHARMACEUTICAL INDUSTRIES LIMITED, Maharashtra (IN)

(*) Notice: Subject to any disclaimer, the term of this patent is extended or adjusted under 35 U.S.C. 154(b) by 0 days.

(21) Appl. No.: 17/564,772

(22) Filed: Dec. 29, 2021

(65) Prior Publication Data

US 2022/0118188 A1  Apr. 21, 2022

Related U.S. Application Data

(60) Division of application No. 17/363,325, filed on Jun. 30, 2021, now Pat. No. 11,246,991, which is a
(Continued)

(30) Foreign Application Priority Data

Sep. 29, 2020  (IN) .............................. 202021042186

(51) Int. Cl.
*A61M 5/315* (2006.01)
*A61M 5/34* (2006.01)
(Continued)

(52) U.S. Cl.
CPC ......... *A61M 5/3155* (2013.01); *A61K 9/0019* (2013.01); *A61K 38/08* (2013.01);
(Continued)

(58) Field of Classification Search
CPC .......... A61M 5/31535; A61M 5/31541; A61M 5/3543; A61M 5/3155; A61M 5/31551;
(Continued)

(56) References Cited

U.S. PATENT DOCUMENTS

| 5,042,977 A | 8/1991 | Bechtold et al. |
| 6,193,698 B1 * | 2/2001 | Kirchhofer ......... A61M 5/3158 604/207 |

(Continued)

FOREIGN PATENT DOCUMENTS

EP  0 496 141 B1  4/1997

*Primary Examiner* — Kami A Bosworth
(74) *Attorney, Agent, or Firm* — Foley & Lardner LLP

(57) ABSTRACT

A method of providing and/or injecting octreotide acetate to a subject in need thereof includes storing the octreotide acetate in a cartridge of a multi-use multi-dose injector provided with a variable dose setter and actuator. The injector includes a needle configured for subcutaneous administration of the octreotide acetate, the octreotide acetate having a concentration of 2,500 μg/mL. The method further includes providing, on the injector, a plurality of indicia only at prescribed doses of 50 μg, 100 μg, 150 μg and 200 μg settable via the dose setter without indicia between said prescribed doses; and permitting setting of a dose of the octreotide acetate by rotation of the variable dose setter, wherein the injector is configured to provide at least one audible feedback during the rotation.

11 Claims, 5 Drawing Sheets

Related U.S. Application Data continuation of application No. 17/087,670, filed on Nov. 3, 2020, now Pat. No. 11,052,196.

(51) Int. Cl.
*A61K 38/08* (2019.01)
*A61K 9/00* (2006.01)

(52) U.S. Cl.
CPC .......... *A61M 5/3158* (2013.01); *A61M 5/347* (2013.01); *A61M 2205/581* (2013.01); *A61M 2210/083* (2013.01); *A61M 2210/086* (2013.01); *A61M 2210/1021* (2013.01)

(58) Field of Classification Search
CPC ............ A61M 5/31553; A61M 5/3156; A61M 5/31561; A61M 5/3158; A61M 5/31593; A61M 2005/3154; A61M 2205/581; A61M 5/31543; A61K 9/0019; A61K 9/0021; A61K 38/08
See application file for complete search history.

(56) References Cited

U.S. PATENT DOCUMENTS

| | | | |
|---|---|---|---|
| 6,200,296 | B1 | 3/2001 | Dibiasi et al. |
| 9,656,023 | B2 | 5/2017 | George et al. |
| 10,272,206 | B2 | 4/2019 | George et al. |
| 10,342,850 | B2 | 7/2019 | Rana et al. |
| 2005/0013840 | A1 | 1/2005 | Potter et al. |
| 2007/0088288 | A1 | 4/2007 | Barron et al. |
| 2013/0303453 | A1 | 11/2013 | Pawar et al. |
| 2014/0213984 | A1 | 7/2014 | Pawar et al. |
| 2015/0224266 | A1 | 8/2015 | Plumptre et al. |
| 2017/0028141 | A1 | 2/2017 | Fiedler et al. |
| 2019/0000918 | A1 | 1/2019 | Rana et al. |

\* cited by examiner

METHOD OF INJECTING OCTREOTIDE ACETATE INTO THE BODY

CROSS-REFERENCE TO RELATED APPLICATIONS

The present application is a divisional of U.S. application Ser. No. 17/363,325 filed Jun. 30, 2021, issued as U.S. Pat. No. 11,246,991 on Feb. 15, 2022, which is a continuation of U.S. application Ser. No. 17/087,670 filed Nov. 3, 2020, issued as U.S. Pat. No. 11,052,196 on Jul. 6, 2021, which claims the benefit of priority to Indian Provisional Application No. 202021042186 filed Sep. 29, 2020, the entire contents of which are incorporated herein by reference.

FIELD

The present disclosure relates to pen-type injectors for injection of octreotide acetate and methods of use thereof.

BACKGROUND

Octreotide acetate, described chemically as L-cysteinamide, D-phenylalanyl-L-cysteinyl-L-phenylalanyl-D-tryptophyl-L-lysyl-L-threonyl-N-[2-hydroxy-1-(hydroxymethyl)propyl]-, cyclic (2 #7)-disulfide; [R—(R*, R*)] acetate salt, is a long-acting octapeptide with pharmacological actions mimicking those of the natural hormone somatostatin. The U.S. Food and Drug Administration approved parenteral product is available under the brand name of Sandostatin® (made by Novartis Pharmaceuticals Corp. of East Hanover, N.J.), which is a clear aqueous preserved solution filled in sterile 5 ml multidose vials in two strengths, 200 ms/ml and 1000 ms/ml.

Octreotide acetate is indicated in the treatment of acromegaly, carcinoid tumors and vasoactive intestinal peptide tumors (VIPomas). In particular, it is indicated for reduction of growth hormone (GH) and insulin-like growth factor 1 (IGF-1) [somatomedin C] in adult patients with acromegaly who have had an inadequate response to or cannot be treated with surgical resection, pituitary irradiation, and bromocriptine mesylate at maximally tolerated doses. Further, octreotide acetate is indicated in the treatment of severe diarrhea/flushing episodes associated with metastatic carcinoid tumors in adult patients, and the treatment of profuse watery diarrhea associated with VIPomas in adult patients.

The dosage and frequency of administration is varied depending upon the indication, but subcutaneous administration is typically performed at least once daily.

SUMMARY

Some embodiments relate to a method of providing octreotide acetate to a subject in need thereof includes storing the octreotide acetate in a cartridge of a multi-use multi-dose injector provided with a variable dose setter and actuator. The injector includes a needle configured for subcutaneous administration of the octreotide acetate, the octreotide acetate having a concentration of 2,500 µg/mL. The method further includes providing, on the injector, a plurality of indicia only at prescribed doses of 50 µg, 100 µg, 150 µg and 200 µg settable via the dose setter without indicia between said prescribed doses; and permitting setting of a dose of the octreotide acetate by rotation of the variable dose setter, wherein the injector is configured to provide at least one audible feedback during the rotation.

In some embodiments, the actuator is operable to discharge the octreotide acetate from the cartridge through the needle.

In some embodiments, a visible surface of the actuator has a first chromatic value, at least a portion of the dose setter surrounding the actuator has a second chromatic value differing from the first chromatic value, and at least a portion of an injector body has a third chromatic value differing from the first chromatic value and the second chromatic value.

In some embodiments, the injector is configured to be primed prior to delivery of a first dose, wherein the priming is carried out by setting the dose setter to a non-zero value and operating the actuator. In some embodiments, the non-zero value is 100 µg.

In some embodiments, the needle comprises a 31 gauge needle having a length of approximately 5 mm and is configured to be threadably connected before use and disconnected and disposed of after use.

In some embodiments, the method further includes arranging the injector such that the needle is insertable into an injection site at 90° relative to the injection site.

In some embodiments, the method includes providing a dose in excess of 200 µg by two or more injections.

In some embodiments, providing the dose comprises turning the dose setter to 200 µg; delivering, to a first injection site, a first injection of 200 µg; turning the dose setter to one of the plurality of indicia; and delivering, to a second injection site differing from the first injection site, a second injection.

In some embodiments, the injector is disposable.

In some embodiments, the indicia are provided so as to correspond to dose volumes of 20 µL, 40 µL, 60 µL and 80 µL.

In some embodiments, the injector is configured to deliver a prescribed dose subcutaneously to one or more of an abdomen, a thigh, or an upper arm of the subject in need thereof.

In some embodiments, the method further comprises providing audible feedback during multiple times and/or in multiple forms during setting of the dose, so as to provide multiple feedbacks.

This summary is illustrative only and should not be regarded as limiting.

BRIEF DESCRIPTION OF THE FIGURES

The disclosure will become more fully understood from the following detailed description, taken in conjunction with the accompanying figures, wherein like reference numerals refer to like elements, in which.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

As utilized herein, the term "patient" means a user for whom octreotide acetate is indicated. The term "patient" is used below in describing exemplary operations involving an injector. However, it should be understood that administration of medicament may be carried out by person(s) other than the patient, e.g., a health care provider or assistant, and so references to a particular actor performing operations are not to be construed as precluding performance by other actor(s).

Referring generally to the figures, an injector device according to one or more embodiments is depicted. As explained below, an injector according to at least one embodiment has features conducive to self-administration by particular patient populations.

Assistive Injector

Assistive technology broadly describes technology that is suited or adapted to particular population groups and their distinct needs. At least one embodiment of a device according to the present disclosure is designed particularly with the needs of patients having acromegaly in mind. Acromegaly is a hormonal disorder including, among its typical symptoms, enlargement of the patient's hands. Such enlargement may impair manual dexterity. Accordingly, typical equipment intended for self-administration of medicament may pose a challenge to such patients. Human factors are of particular relevance where side effects or other undesirable consequences may be associated with improper drug delivery. Furthermore, such factors are of particular importance in self-administration of medicament, e.g., for chronic conditions where a patient is performing multiple such injections rather than visit a healthcare provider.

In at least one embodiment, a self-administrable injector device is provided which may be particularly conductive to patients with impaired dexterity associated with acromegaly, for example. The device is not limited to use by patients with acromegaly. The usability of the injector facilitates repeatable self-administration by patients for whom octreotide acetate is indicated.

Figure 1:
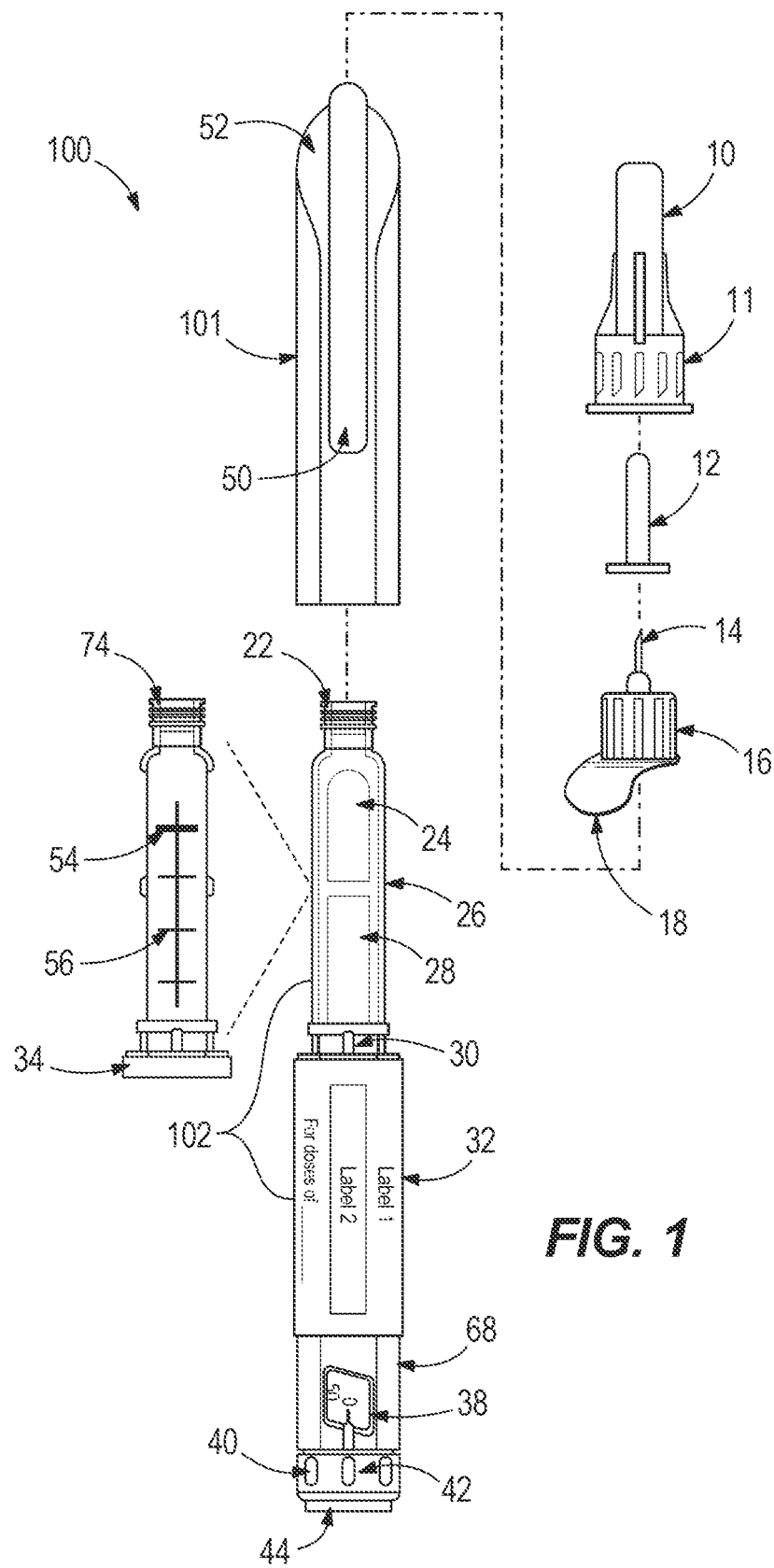
FIG. 1 is an exploded view of an injector in accordance with some embodiments.
Figure 2A:
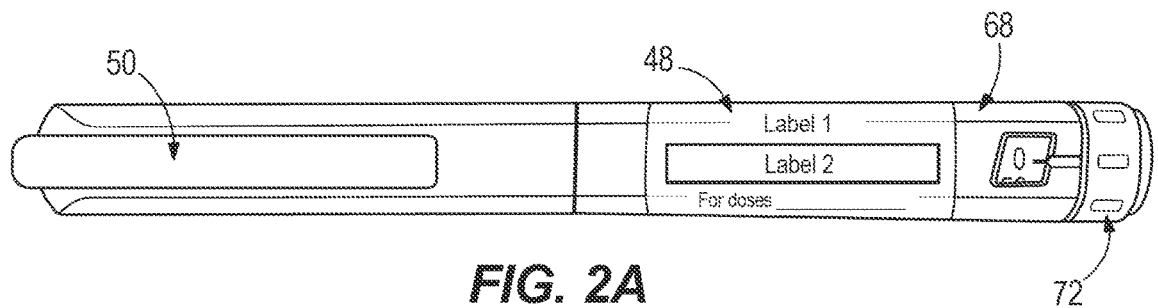
FIG. 2A is a top view of an injector in accordance with some embodiments.
Figure 2B:
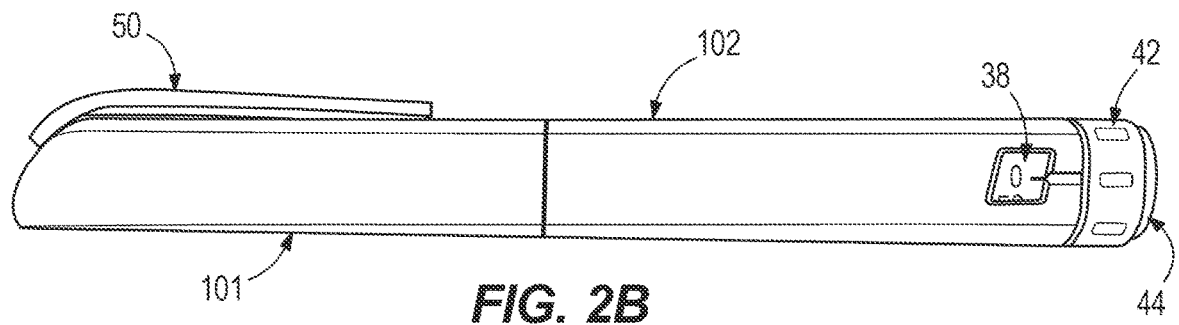
FIG. 2B is a side view of the injector shown in FIG. 2A in accordance with some embodiments.
Figure 2C:
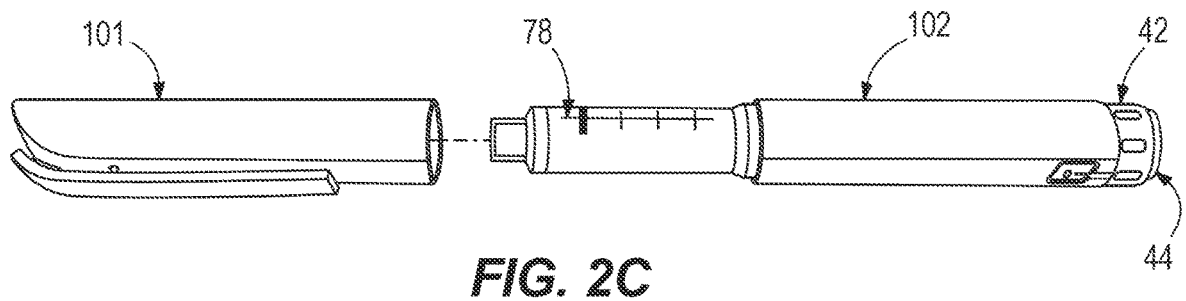
FIG. 2C is another side view of the injector shown in FIG. 2A in accordance with some embodiments.

With reference to FIG. 1, an exemplary process and device for administering octreotide acetate are described in accordance with at least one embodiment. The administration may be self-administration, e.g., when the patient uses the injector shown in FIG. 1 to inject the octreotide acetate at an injection site of the patient. FIGS. 2A-2C depict an exemplary device for administering octreotide acetate in accordance with at least one embodiment. In particular, FIG. 2A depicts a top view of such a device, and FIG. 2B and FIG. 2C depict side views of such a device.

Figure 5A:
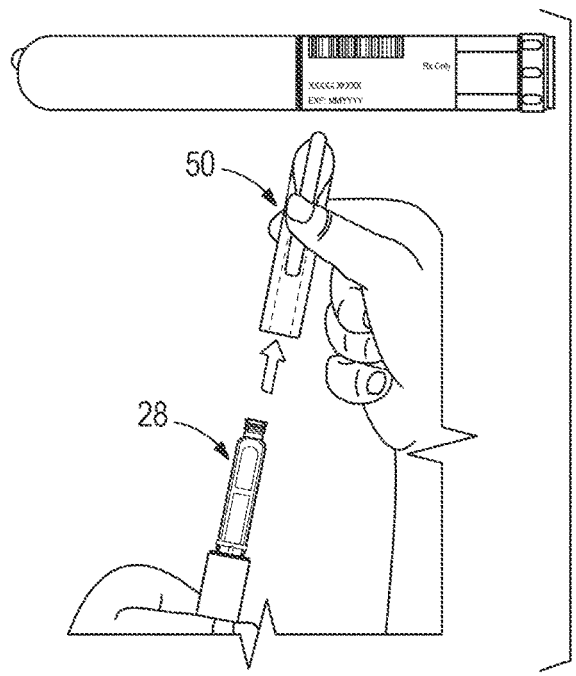
FIG. 5A is a depiction of at least one first operation carried out for administration of octreotide acetate in accordance with some embodiments.

FIG. 1 depicts an injector 100 in accordance with at least one embodiment. To use the injector 100, a patient removes cap 101 from injector body 102. To facilitate removal of the cap 101 and/or replacement of the cap 101 onto the body 102, the cap 101 may be provided with a bar or clip 50 to which force may be applied by the patient's finger(s) while gripping the cap 101 to dislodge the cap 101 from the body 102. The cap 101 may be provided with a rounded profile 52 having at least a partially ovoid contour configured to be contacted by a patient's finger(s) when the patient is removing the cap 101 from body 102 or returning the cap 101 in place. The bar 50 and/or profile 52 may facilitate pulling the cap 101 off the body 102 in a linear pulling motion, without twisting or turning of cap 101, as indicated by the upward-pointing arrow in FIG. 5A. This may be more easily carried out by patients with acromegaly than more complex cap-removal operations, for example.

Once the cap 101 is removed from body 102, a seal 22 at one end of the injector 100 is exposed. The seal 22 may be a rubber seal configured to inhibit ingress of contaminants into body 102. The seal 22 may be cleaned with an alcohol swab before a needle 14 is attached to body 102.

Needle

In some embodiments, a needle 14 is provided separately from the injector 100 for attachment to the injector 100 prior to administration of medicament. In some embodiments, the needle may have a gauge of from 29 to 32 (29G to 32G). The needle may be a 31 gauge (31G) needle, for example. In particular, a 31 gauge disposable pen needle of about 5 mm in length may be used, in some embodiments.

Figure 5B:
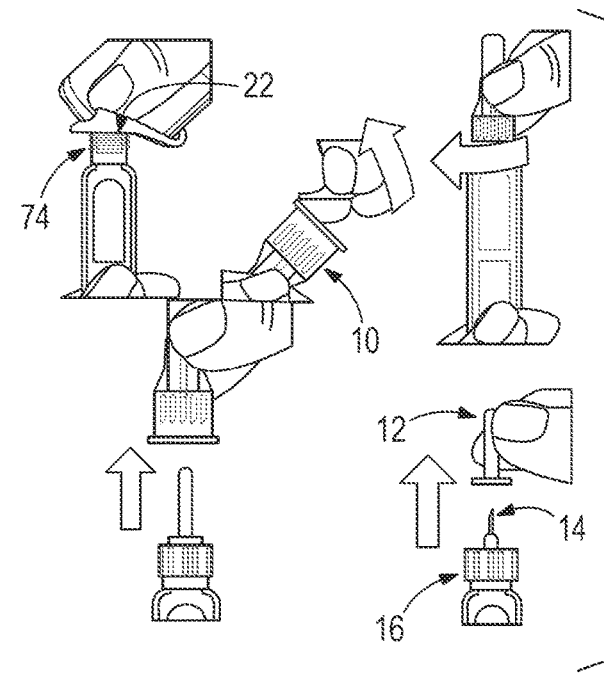
FIG. 5B is a depiction of at least one second operation carried out for administration of octreotide acetate in accordance with some embodiments.

In some embodiments, the needle 14 may be provided with an outer needle cover 10, an inner needle cover 12, and a tab 18 shown in FIG. 1 and FIG. 5B, for example. The tab 18 may be a paper tab that is readily peeled off from the outer cover 10. Once removed, the outer cover 10 containing the needle 14 therein may be pushed onto the body 102 and coupled to the body 102, e.g., by fastening via a threaded fit between the body 102 and the outer cover 10.

For example, in some embodiments, the outer cover 10 covering needle 14 may be screwed clockwise onto coupling portion 74 (a coupler) of a cartridge holder 26 until the outer cover 10 is securely coupled to the body 102. The coupling portion 74, shown in FIG. 5B, for example, may include threading configured to mate with corresponding threaded portion 16. In particular, the needle 14 may be threadably connected via its cover 10 to the coupling portion 74 before injection and then disconnected and disposed of afterwards.

Prior to injection, the outer needle cover 10 may be removed and set aside to later be placed back on the needle 14 to facilitate safe detachment of the needle 14 from the body 102. Further, after removing the outer needle cover 10, the inner needle cover 12 may then be removed. In contrast to the outer needle cover 10, the inner needle cover 12 may be discarded and not returned to position following injection.

Pre-Injection and Priming

In some embodiments, before use of the injector, the injector is refrigerated at about 2° C. to about 8° C. (about 36° F. to about 46° F.) in its original packaging. The injector is preferably protected from natural light when stored. After the injector is used for the first time, it is stored at a controlled room temperature between about 20° C. to about 25° C. (about 68° F. to about 77° F.). In some embodiments, the injector is configured to remain usable when maintained between about 15° C. to about 30° C. (about 59° F. to about 86° F.) for at least twenty-eight (28) days. In some embodiments, the patient is instructed to discard the injector twenty-eight days after first use.

In advance of injection, the injector 100 may be primed as described herein. Priming according to the techniques described below may result in reduced likelihood of air injection or an improper dose (e.g., a partial, too-small dose). Before priming the injector 100, the injector 100 may be inspected visually for particulate matter and discoloration. The injector 100 may be at room temperature prior to injection. If the injector 100 was refrigerated, for example, then the injector 100 may be kept at room temperature for about 20 minutes to about 30 minutes prior to injection.

To prime the injector 100, dose setter 42 and actuator 44 are operated in turn. The dose setter 42 may be a variable dose setting mechanism allowing for selection among a plurality of doses. In some embodiments, dose setter 42 may be manipulated by manual rotation such that a dose is set to an initial priming dose value (e.g., about 100 µg). More particularly, the dose setter 42 may be rotated until the hatch mark 60 visible through a window 38 corresponds to a 100 µg dose. The dose setter 42 may be operated to be movable such that the patient may select one of a plurality of doses for administration.

Figure 3A:
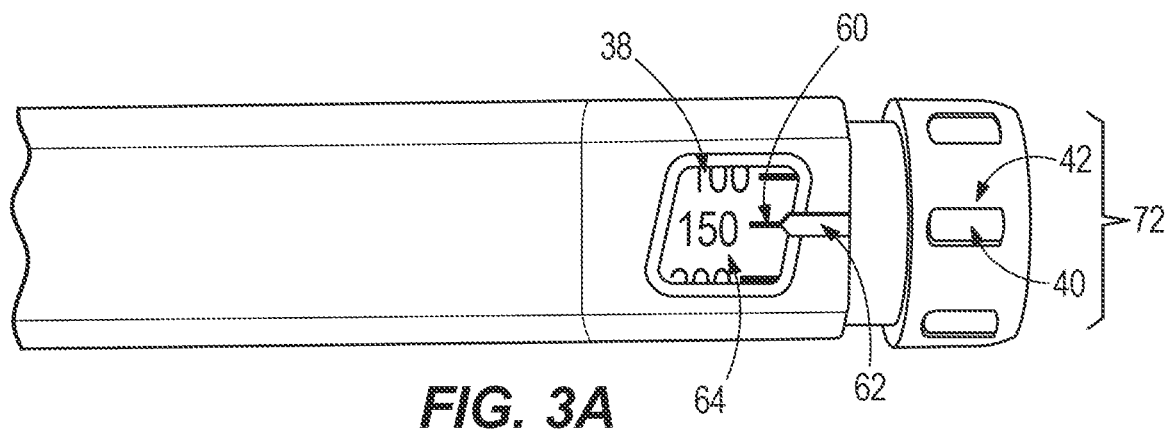
FIG. 3A is a detail view of a portion of an injector in accordance with some embodiments.
Figure 3B:
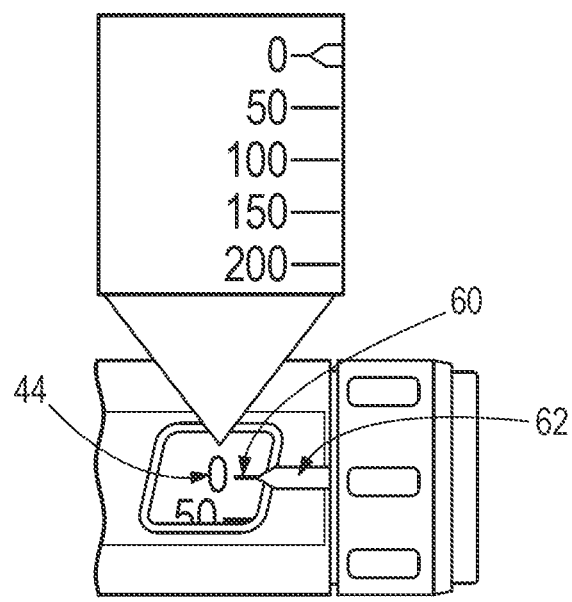
FIG. 3B is a schematic detail view of a portion of an injector in accordance with some embodiments.

As shown in FIG. 3A, for example, when the patient manipulates the dose setter 42 to cause the dosage hatch mark 60 to align with dose indicator 62, which may serve as a pointer, the numerical dose value displayed to the left of hatch mark 60 corresponds to the dosage to be delivered. In FIG. 3A, by way of example, the hatch mark 60 has to its left a numerical dose value 64 of 150, indicating that a 150 µg dose of octreotide acetate is to be provided. In some embodiments, the numerical dose values 64 are provided so as to correspond to dose volumes of 20 µL, 40 µL, 60 µL and 80 µL. As shown in FIG. 3B, the indicated values may be, for example, in 50 µg increments, up to 200 µg, in some embodiments.

In some embodiments, numerical dose values 64 may be substituted and/or combined with other indications of dosage, e.g., "low," "medium," or "high" dosage amounts, for example, and alphanumeric content may be displayed alternatively or in addition to the numerical dose value(s). In some embodiments, window 38 and numerical dose values 64 are configured such that only one numerical dose value 64 is visible in its entirety (e.g., completely legible without truncation) in the window 38. For example, a patient may view a portion of a numerical dose value 64 at one or more edges of window 38, but only a single numerical dose value 64 may be visible in full, so as to further confirm to the patient that the depicted numerical dose value 64 is the dose to be delivered.

Figure 5C:
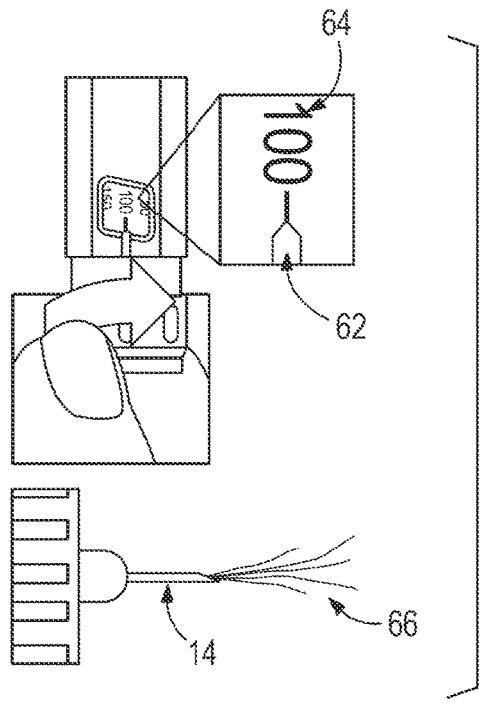
FIG. 5C is a depiction of at least one third operation carried out for administration of octreotide acetate in accordance with some embodiments.

In some embodiments, the numerical dose value 64 used for priming may be a non-zero value, e.g., 100 µg, as shown in FIG. 5C. Following setting by the dose setter 42 to 100 µg, for example, priming is continued. To continue priming the injector 100, the injector body 102 is held with the needle 14 pointing upward. An injector actuator 44 is then activated to cause medicament to be delivered through the needle 14. In some embodiments, the actuator 44 is a button provided at a side of dose setter 42 and at a distal end of body 102, with at least a portion of dose setter 42 surrounding at least part of actuator 44. The actuator 44 may be attached to the dose setter 42. In some embodiments, the button may be slid along a part of dose setter 42 and/or injector body 102 to actuate delivery of medicament. Alternatively, in some embodiments, a clip may be provided in lieu of a button.

The actuator 44 is configured such that actuation thereof moves a plunger in the body 102 to deliver medicament to needle 14. In some embodiments, a plume or spray 66 of medicament is ejected via the needle 14 when priming, as shown in FIG. 5C. In some embodiments, the actuator 44 is actuated (e.g., by pressure exerted by the patient's finger(s)) fully, so that the numerical dose value 64 changes from the set dose (e.g., 100 µg) to a zero value. In at least one embodiment, priming is performed at the beginning of each session or treatment period when one or more injections are performed. However, priming is not repeated before every injection or routine use, but rather only performed once at the beginning of a session or treatment period when one or multiple injections are performed with a new injector in first use. In this manner, medicament in the injector 100 may be conserved.

Injection Site

Following priming, an injection site 76 may then be selected for the patient. Exemplary injection sites 76 are depicted in FIG. 5E. For example, where the injection site is the abdomen, the injection site may be at least two inches away from the patient's navel. When the injection site is the patient's thigh(s), the injection site may be the front, middle portion of the thigh(s). When the patient is not self-administering but instead receiving assistance (e.g., through a health care provider or layperson assisting the patient), the injection site may be the back, outer area of the upper arms, for example.

In some embodiments, the injection may be administered to one or more of a patient's abdomen, thighs, or the dorsal or outer areas of the upper arms, as indicated by the highlighted areas of FIG. 5E. The method of administering the octreotide acetate may include rotating the injection site so that the same site is not used for consecutive injections. The method may include spacing a subsequent injection site at least two inches from an immediately previous injection site. Once the injection site is selected, the site may then be prepared for injection, e.g., by cleaning with an alcohol swab and allowing the site to dry before injection.

Dose Setting

In some embodiments, once the injection site is prepared, the dose setter 42 may then be operated so that the numerical dose value 64 appearing in window 38 is a desired dose (e.g., the prescribed dose). In some embodiments, the dose numerical value 64 is aligned so as to be co-axial with the hatch mark 60 and the dose indicator 62 to indicate that the dose is set to the prescribed dose. In some embodiments, the dose numerical value 64, the hatch mark 60, the dose indicator 62 and at least one recess or groove 40 of the dose setter 42 may all be co-axially aligned when the dose is set.

As shown in FIG. 3A, the dose setter 42 may be configured as a rotatable body 72 having a plurality of recesses or grooves 40. In some embodiments, the dose setter 42 may not be rotatable and may allow for selection of a dose via another operation, e.g., by pulling. In some embodiments, dose setter 42 may be both rotated and pulled to select and set a dose.

In some embodiments, the numerical dose values 64 correspond to dosages of 50 µg, 100 µg, 150 µg and 200 µg, and a dose value 64 of 0 µg. In some embodiments, the hatch marks 60 are provided only where the numerical dose values 64 are present and no other markings appear in the window 38 other than the numerical dose values 64 and the hatch marks 60. For example, no indicia between the prescribed doses are present. The absence of extraneous indicia—e.g., indicia that do not correspond to any prescribed dose—may contribute to reduced confusion and reduced dosing error.

Injection

In some embodiments, once the numerical dose value 64 appears in the window 38 and is aligned with indicator 62, the dose may then be delivered by activating the actuator 44. In particular, the injector 100 may be positioned such that the needle 14 is insertable into the selected injection site at an angle of 90° relative to the injection site and the actuator 44 is actuated. For example, the actuator 44 may be depressed to a maximum extent, until actuator 44 stops movement. In some embodiments, the numerical dose value 64 in the window 38 transitions from the desired or prescribed dose (a non-zero value) to a zero value when the injection is complete, indicating that the full dosage has been administered.

Accordingly, the appearance of a "zero" value for numerical dose value 64 indicates that administration of the dose is complete. Once the numerical dose value becomes zero, the actuator 44 may be kept in a depressed state for a given time period, e.g., about ten seconds, to aid in ensuring delivery of the full amount of the dose. In particular, the user may be instructed to press the actuator 44 and maintain pressure (e.g., manually, as exerted by the user's finger or thumb, for example) while waiting until ten seconds have elapsed). Following elapse of the time period, the injector 100 may be lifted directly upward from the injection site.

Figure 5D:
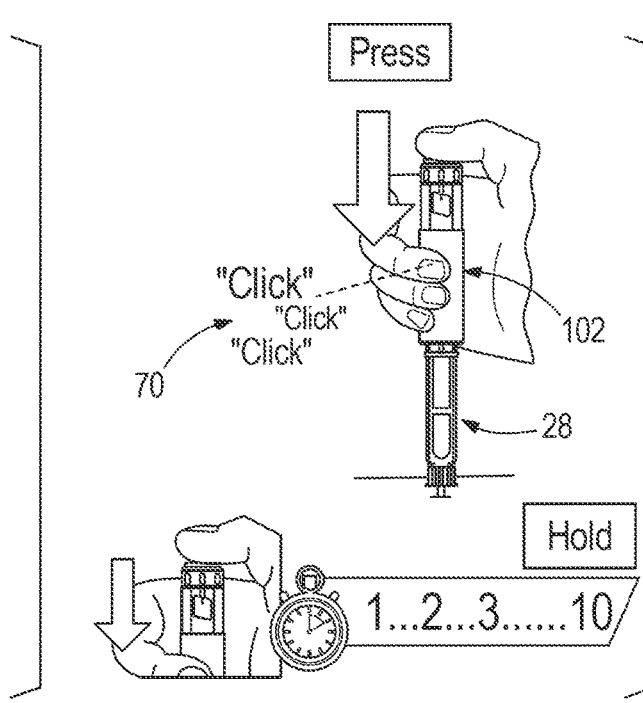
FIG. 5D is a depiction of at least one fourth operation carried out for administration of octreotide acetate in accordance with some embodiments.
Figure 5E:
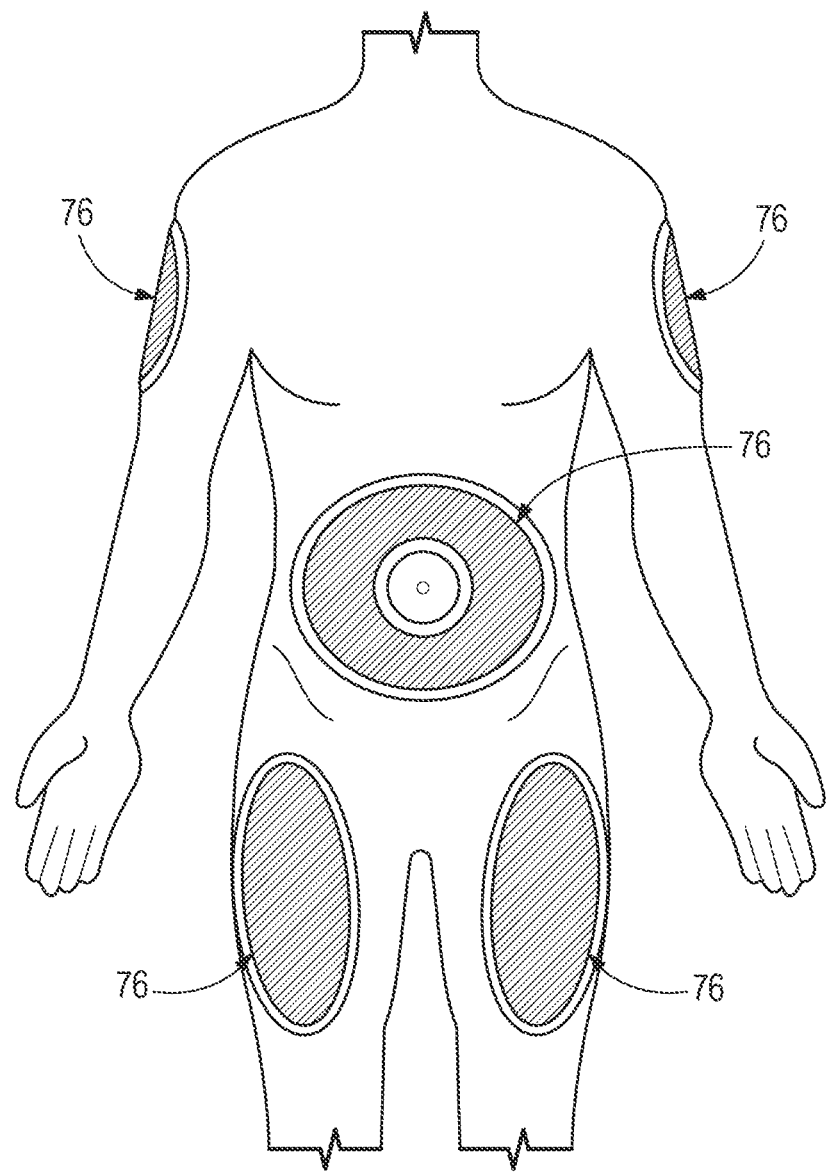
FIG. 5E depicts exemplary injection sites to which octreotide acetate may be injected in accordance with some embodiments.

In addition, in some embodiments, feedback may be provided during the setting of the dose and/or the injection, as indicated in FIG. 5D. For example, a clicking noise may be emitted when the dose setter 42 is operated. In some embodiments, a portion of the body 72 of dose setter 42 may engage with a portion of the injector body 102 so as to emit one click per one rotation or partial rotation of the dose setter 42, for example. That is, when the dose setter 42 is operated, the body 72 engages to produce audible feedback. For example, in some embodiments, a noise may be emitted each time one of the recesses or grooves 40 of dose setter 42 is moved, such that multiple instances of audible feedback occur during dose setting.

Exemplary dosages and concentrations may differ in various embodiments. In some embodiments, medicament may be provided in the form of sterile 1-mL ampoules in three strengths, containing 50 µg, 100 µg, or 500 µg octreotide (as acetate), and sterile 5-mL multi-dose vials in two strengths, containing 200 µg/mL or 1000 µg/mL of octreotide (as acetate).

In some embodiments, treatment of a patient with acromegaly may include providing a dose of about 50 µg three times daily or 100 µg three times daily. In some embodiments, treatment of a patient with carcinoid tumors may include providing a dose of about 100 µg daily to about 600 µg daily divided into 2-4 doses, e.g., for a first two week period.

For example, the mean daily dose may be about 300 µg. In some embodiments, the median daily dose may be about 450 µg. In some embodiments, the daily dose may be about 750 µg to about 1,500 µg. In some embodiments, treatment of a patient with VIPomas may include providing a dose, e.g., for a first two week period, of about 200 µg daily to about 300 daily, divided into 2 to 4 doses. The daily dosage in some embodiments may be about 150 µg to about 750 µg.

In some embodiments, the concentration of octreotide acetate in the injector may be about 2,500 µg/mL. The deliverable volume of the injector is about 2.8 mL. In some embodiments, each milliliter of the solution may contain about 2,500 µg octreotide (present as octreotide acetate, USP) (i.e., 2,500 µg/mL), about 3.4 mg lactic acid USP, about 22.5 mg mannitol USP, about 5 mg phenol USP, and water for injection USP. In some embodiments, the pH of the solution may be about 4.2±0.3 by the addition of aqueous sodium bicarbonate solution.

After subcutaneous injection, octreotide may be absorbed completely from the injection site. Peak concentrations of about 5.2 ng/mL (for a dose of 100 µg) were reached 0.4 hours after dosing. Peak concentrations and area under the curve values may be dose proportional after subcutaneous single doses up to 500 µg and after subcutaneous multiple doses up to 500 µg three times a day (1,500 µg/day). The distribution of octreotide from plasma may be rapid (e.g., $t\alpha\frac{1}{2}=0.2$ h), the volume of distribution (Vdss) may be about 13.6 L, and the total body clearance may be about 7 L/hr to about 10 L/hr. In blood, the distribution into the erythrocytes was found to be negligible and about 65% was bound in the plasma in a concentration-independent manner. For patients with acromegaly, there may be a different pharmacokinetic profile. For example, a mean peak concentration of about 2.8 ng/mL (100 µg dose) may be reached in about 0.7 hours after subcutaneous dosing, and the volume of distribution (Vdss) may be about 21.6±8.5 L, with the total body clearance increased to about 18 L/hr, and the mean percent of the drug bound being about 41.2%.

Cartridge

In some embodiments, the injector 100 may include a cartridge holder 26 configured to store therein a cartridge 28 containing octreotide acetate. The cartridge holder 26 may be connected to the injector body 102 at one or more flanges 30. The cartridge holder 26 may be separated from a terminal portion 68 of the injector body 102 by a central body portion 32. In some embodiments, the cartridge holder 26 may have a base portion 34 where the cartridge holder 26 is coupled to the central body portion 32 of injector body 102. In particular, base portion 34 may have threading (e.g., male threads) to facilitate coupling to the central body portion 32.

In some embodiments, the cartridge holder 26 may be formed as a frame having cutouts 24 which are visible portions allowing for viewing of at least part of the cartridge 28. The cartridge 28 may be made of translucent or semi-translucent material, permitting the patient to view the contents of the cartridge 28. Further, together with the cartridge 28, the cutouts 24 allow the patient to ascertain visually whether the medicament appears clouded or otherwise potentially contaminated, for example. Further, in some embodiments, the injector body 102 may include a label 48 containing information such as an expiration date. Thus, visual inspection of the cartridge contents and the label information may indicate whether the contents are contaminated and/or expired. Additionally, the central body portion 32 may be provided with additional labeling that may be applied thereto, such as first and second labels.

Additional Features

As noted above, in some embodiments, injector 100 may be provided with features to aid in administration or self-administration, so as to promote ease of use by particular patient populations. In some embodiments, the injector 100 is configured with features to enhance visibility and/or contrast of components to promote proper use and administration of medicament. For example, a terminal portion 68 of injector body 102 containing window 38 may be provided in a different, contrasting color from the window 38 itself.

In some embodiments, a visible surface of the actuator 44 has a first chromatic value, at least a portion of the dose setter 42 surrounding the actuator 44 has a second chromatic value differing from the first chromatic value, and at least a portion of an injector body 102 has a third chromatic value differing from the first chromatic value and the second chromatic value. For example, as appreciated from FIGS. 2A and 2B, the actuator 44 has a first chromatic value that is darker than that of the body 72 of dose setter 42 (including the portion of the dose setter 42 visible in window 38) having a second chromatic value, and the terminal portion 68 of injector body 102 has a third chromatic value differing from both the first and second chromatic values. In some embodiments, the terminal portion 68 may be blue, the window 38 may be white, and the actuator 44 may be black, for example. In some embodiments, various components may differ in one or more of a chromatic value or achromatic value from each other, such that at least the terminal portion 68, the window 38 and actuator 44 may differ from one or more of each other in terms of chromatic or achromatic value. In some embodiments, the differing chromatic/achromatic values contribute to particular components that may be easily visually perceived and distinguished from each other (e.g., by appearance alone).

Further, the contrast of one or more components next to one or more neighboring components may be such that a patient with dexterity impairments or other conditions may quickly and easily identify portions of the injector 100, and may reduce the likelihood of misuse. In some embodiments, window 38 may be constructed to have a shape differing from neighboring components so as to heighten visual contrast and aid in identification of the window 38. For example, as shown in FIGS. 2A and 2B (in addition to other figures), the window 38 may be configured as a parallelogram. Additionally, the portion of the injector 100 containing the numerical dose value 64 and hatch marks 60 may be provided at a different height relative to the terminal portion 68, such that the portion containing the dose value 64 and hatch marks 60 is slightly recessed relative to an outermost surface of terminal portion 68, for further differentiation.

In some embodiments, the injector 100 is configured to provide an indication as to when it is approaching empty. For example, the injector 100 may provide an indication when the contents of medicament in the injector 100 are reaching or at a level insufficient to provide a desired dose or multiple doses. In some embodiments, for example, when the plunger moves past indicium 54 in the axial direction of the injector 100, the injector 100 is at or approaching empty. In some embodiments, when the injector 100 is used multiple times and a substantial amount of medicament is delivered, the plunger may extend toward or beyond the indicium 54 toward seal 22.

Figure 4:
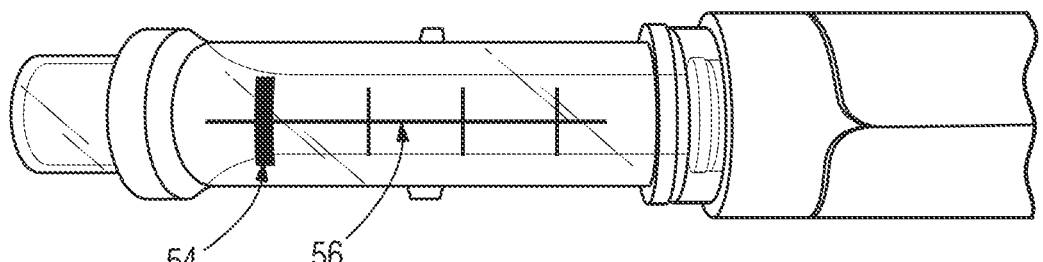
FIG. 4 is a detail view of a portion of an injector in accordance with some embodiments.

As shown in FIG. 4, indicium 54 is configured to be visually distinct from other indicia 56 which may be shown as hatch marks having a lighter line weight than indicium 54 and provided along marking line 78, in some embodiments. Further, in some embodiments, when rotation of knob 42 is prohibited, then the injector 100 is at or approaching empty. In some embodiments, the movement of the plunger beyond indicator 54 and the prevention of rotation of knob 42 both signify that the injector 100 is at or approaching empty.

In some embodiments, accidental overdosing and/or underdosing may be addressed according to the techniques described below. For example, if the dose setter 42 is set to a higher dose than what is prescribed, the dose setter 42 may be operated to re-set the dose to the prescribed value. For example, when the dose setter is a rotatable body 72 as shown in FIG. 3A, the body 72 may be turned until the numerical dose value 64 of the prescribed dose appears in window 38. In some embodiments, the dose setter 42 may include a rotatable element such as rotatable body 72 which may be rotated and then pulled (e.g., pulled in an axial direction) to set a dose. For example, at least a portion of dose setter 42 may be rotated to select a dose, and then pulled to set the selected dose (e.g., by pulling in an axial direction and opposite to a direction of extension of needle 14).

Further, in some embodiments, underdosing may be remedied by providing a second injection of an amount corresponding to the difference between the prescribed dose and the delivered dose. Additionally, in some embodiments, a dose in excess of the maximum numerical dose value 64 may be provided in the following manner. First, the dose setter 42 is set to the maximum dose setting (e.g., such that numerical dose value 64 corresponds to 200 µg). Second, the maximum dose is administered. Third, a second injection site is selected in accordance with the techniques described above. Fourth, a remaining dose is determined as the prescribed dose less the maximum dose (i.e., the previously administered dose). If the remaining dose is greater than the maximum dose setting, then once again, the numerical dose value 64 would be set to the maximum setting. The remaining dose is then administered. This process may then be iterated until the prescribed dose is administered.

Reusability

In some embodiments, the injector 100 is a disposable injector intended to be discarded after each use. On the other hand, in some embodiments, injector 100 may be configured for multiple, repeated usage by a patient. For example, following initial use of the injector 100, the outer needle cover 10 is placed on a flat surface. The injector body 102 is configured to be held, in one hand of the patient with the needle 14 attached thereto, such that the needle 14 may then be inserted into the outer cover 10 without using the other hand. The outer cover 10 may then be pushed against the body 102 to ensure that the outer cover 10 is snugly positioned on the needle 14. The inner needle cover 12 is not placed back on the needle 14.

Once the outer cover 10 is positioned on the needle 14, the user may then decouple (detach) the needle 14 (as covered by outer cover 10) from the body 102 of injector 100. For example, the covered needle 14 may be unscrewed from coupling portion 74. The patient may squeeze a lower portion 11 of the outer cover 10 covering needle 14, while turning lower portion 11 (e.g., counterclockwise). The lower portion 11 may be provided with grooves or ridges that contact against or engage threading portion 16, as shown in FIG. 1. In particular, the ridges may slide over the threading portion 16. In some embodiments, the threading portion 16 may be provided with female threads that mate to male threads of coupling portion 74 of the cartridge holder 26.

The covered needle 14 then detaches from the body 102 due to the decoupling motion and may be removed and discarded. Once the covered needle 14 is so removed, the cap 101 may then be placed back on the body 102. With the cap 102 back on the body 101, the used injector 100 may then be stored at room temperature between about 20° C. to about 25° C. (about 68° F. to about 77° F.) or in a refrigerator refrigerated between about 2° C. to about 8° C. (about 36° F. to about 46° F.) for up to twenty-eight days.

Following injection, the injection site may be cleaned by pressing with a cotton ball or alcohol swab, for example. Further, in some embodiments, the exterior of the injector may be cleaned by wiping with a damp cloth. A cleaning solution containing alcohol may be used.

As utilized herein with respect to numerical ranges, the terms "approximately," "about," "substantially," and similar terms generally mean +/−10% of the disclosed values, unless specified otherwise. As utilized herein with respect to structural features (e.g., to describe shape, size, orientation, direction, relative position, etc.), the terms "approximately," "about," "substantially," and similar terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic, or combinations thereof.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above.

It is important to note that any element disclosed in one embodiment may be incorporated or utilized with any other embodiment disclosed herein and that various modifications may be made. For example, different surface textures may be utilized in connection with different colors for one or more portions of the injector according to various embodiments. It should be appreciated that various elements of certain embodiments may be incorporated or utilized with any of the other embodiments disclosed herein.

What is claimed is:

1. A method of treating one or more of acromegaly, carcinoid tumors or vasoactive intestinal peptide tumors by providing and/or injecting octreotide acetate for a subject in need thereof, comprising:
    storing the octreotide acetate in a cartridge of a multi-use multi-dose injector provided with a variable dose setter and an actuator, the injector comprising a needle configured for subcutaneous administration of the octreotide acetate, the octreotide acetate having a concentration of about 2,500 µg/mL;
    permitting setting of a dose of the octreotide acetate by rotation of the variable dose setter to one of a plurality of indicia of prescribed doses, wherein there are no indicia between the indicia of the prescribed doses, wherein the injector is configured to provide at least one audible feedback during the rotation of the dose setter, and wherein the actuator is operable to discharge the octreotide acetate from the cartridge through the needle; and
    providing a daily dose of up to about 1,500 µg in two or more sessions, wherein the two or more sessions comprise a first session and a second session;
    in the first session, providing a dose in excess of a maximum dose setting by two or more injections, comprising
        turning the dose setter to the maximum dose setting;
        delivering, to a first injection site, a first injection at the maximum dose setting;
        turning the dose setter to one of the plurality of indicia; and
        delivering, to a second injection site differing from the first injection site, a second injection,
        wherein the injector is configured to correct for overdosing by allowing, after the dose setter is set to a dose higher than a desired dose setting, rotation of the dose setter to re-set the dose setter to a prescribed dose among the prescribed doses.

2. The method of claim 1, wherein the maximum dose setting is 200 µg.

3. The method of claim 1, wherein the injector comprises a re-attachable cap configured for multi-use injection.

4. The method of claim 1, wherein the method further comprises:
    in the second session,
        turning the dose setter to the maximum dose setting;
        delivering, to a third injection site, a third injection at the maximum dose setting;
        turning the dose setter to one of the plurality of indicia; and
        delivering, to a fourth injection site differing from the third injection site, a fourth injection.

5. The method of claim 1, wherein the prescribed dose is 50 µg, 100 µg, 150 µg or 200 µg.

6. The method of claim 1, wherein the injector is configured to be held in one hand of the subject with the needle attached to the injector, and is further configured such that the needle is insertable into a needle cover without utilizing another hand of the subject.

7. The method of claim 1, further comprising turning a body of the injector until one of the plurality of indicia corresponding to one of the prescribed doses appears in a window of the injector.

8. The method of claim 1, wherein re-setting the dose comprises rotation of the dose setter until the prescribed dose appears in a window of the injector.

9. The method of claim 1, wherein the first injection is followed in succession by the second injection.

10. The method of claim 1, wherein all of the daily dose is delivered during the two or more sessions, the two or more sessions consisting of the first session and the second session.

11. The method of claim 1, wherein the prescribed doses consist of a 50 µg dose, a 100 µg dose, a 150 µg dose, and a 200 µg dose.

* * * * *